US005092322A

United States Patent [19]

Gantz

[11] Patent Number: 5,092,322

[45] Date of Patent: Mar. 3, 1992

[54] PATIENT-CONTROLLED TRACTION DEVICE

[75] Inventor: William A. Gantz, Alameda, Calif.

[73] Assignee: Scott Berglin, Hayward, Calif.

[21] Appl. No.: 574,060

[22] Filed: Aug. 29, 1990

[51] Int. Cl.[5] .......... A61F 5/04

[52] U.S. Cl. .......... 602/35; 602/33

[58] Field of Search .......... 128/84 R, 84 A, 84 C, 128/84 B, 87 R, 87 A, 77, 75, 85; 269/328

[56] References Cited

U.S. PATENT DOCUMENTS

| | | | |
|---|---|---|---|
| 2,871,853 | 2/1959 | Demarest | 128/84 R |
| 3,616,795 | 11/1971 | Powlan | 128/85 |
| 3,847,146 | 11/1974 | Cushman | 128/75 |
| 3,888,243 | 6/1975 | Powlan | 128/84 C |
| 3,910,263 | 10/1975 | Wallander | 128/75 |
| 3,937,216 | 2/1976 | Brown | 128/84 C |
| 4,266,537 | 5/1981 | Bonin, Jr. | 128/75 |
| 4,323,060 | 4/1982 | Pecheux | 128/84 R |
| 4,365,623 | 12/1982 | Wilhelm | 128/75 |
| 4,583,532 | 4/1986 | Jones | 128/75 |
| 4,768,498 | 9/1988 | Herrick | 128/75 |

*Primary Examiner*—Robert A. Hafer

*Assistant Examiner*—Michael Brown

*Attorney, Agent, or Firm*—Thomas M. Freiburger

[57] ABSTRACT

A device for traction medical therapy exerts a force on the patient as selected via a patient or doctor-controlled hand-held unit. The unit sends signals to a traction puller device which may be secured to the end of the patient's bed, or on some other appropriate framework. Traction force is developed by a small fluid pump, preferably a vacuum pump, acting to evacuate a cylinder with a piston which is connected to a traction pulling line or cord connected to the patient. The patient can increase the traction force by further evacuation of the cylinder, and can lighten traction force by operating a valve which gradually vents vacuum from the system. In a preferred embodiment, the piston and cylinder have a rolling diaphragm, making the cylinder completely leak proof so that traction force will not dissipate over time. Another preferred feature is the inclusion of a differential controller which enables a traction patient to selectively set a given pulling force for the apparatus, regardless of movements of the patient which would otherwise tighten or slacken the traction line.

10 Claims, 5 Drawing Sheets

PATIENT-CONTROLLED TRACTION DEVICE

BACKGROUND OF THE INVENTION

This invention is in the field of medical therapy equipment, and particularly relates to equipment for maintaining traction on a patient, for treating back, hip, leg and other injuries.

Patient traction has generally been accomplished with weights. If a traction force of ten pounds, for example, is prescribed for a patient, a ten pound weight is used. The weights are attached to one or more ropes or lines engaged over pulleys.

While this conventional system of weight-imposed traction is simple in concept and has been relatively effective, it has had several shortcomings. If the traction force is to be adjusted, more or fewer weights must be attached to the traction line, and a set of weights of various sizes must be kept for this purpose. Also, certain types of traction require the pulling force to be applied from an unusual angle, so that a longer line is required, along with an elevated pulley. Two pulleys may be required to avoid having the weights in an obtrusive position. The tension rope may stretch along several lines, reducing somewhat access to the patient. Also, weight-imposed traction apparatus is not easily portable, requiring rather complex setup of the frame and pulley apparatus.

Further, it is often required that the traction pulling force be adjusted, particularly to alleviate patient discomfort. With the system of weights and pulleys, this requires the assistance of an attending physician or nurse, who might not always be readily available. It is not possible in most circumstances for the patient to adjust the traction weights.

Some forms of electromechanical traction devices have also been known and used. In one type of mechanical traction unit, a motorized device was settable to exert a traction pulling force on a patient intermittently. However, the unit was not as versatile and fail-safe as the device of the present invention, and it was not controllable by the patient.

It is an object of the invention described herein to overcome these problems and to provide a simple but automated traction pulling device which is very easily adjusted, by either an attending doctor or professional or by the patient himself, to increase or decrease traction force or to induce a selected numerical level of traction force.

SUMMARY OF THE INVENTION

The present invention is an automatic and continuously adjustable traction force unit for traction patients. It can replace fairly intricate systems of ropes and pulleys and framework that are sometimes required over and about the bed for conventional weight and pulley traction. In a preferred embodiment the pulling force of the unit is supplied by a vacuum cylinder which preferably uses a rolling diaphragm type piston and cylinder arrangement. This is advantageous over sliding friction seals in that air leakage can be totally prevented and friction is nearly eliminated.

A small vacuum pump, which may be an aquarium type pump developing about ½ torr, is used to evacuate the cylinder. This provides an absolute fail-safe feature that prevents overpulling against the patient. The pump itself can only draw a certain vacuum, and the cylinder is of course limited to an absolute vacuum at any rate, putting an absolute upper limit on the pulling force which can be developed. Air pressure can be used instead of vacuum, if desired, but vacuum enables a simpler pulling system with no sealing required at the traction line side. Also, it is inherently fail-safe against overpulling, as outlined above.

At the outer side of the cylinder and connected to the piston is a rope or line to be connected to the patient. This can have a motion multiplier, i.e. a block and tackle arrangement which multiplies the amount of motion and therefore reduces the pulling force by a similar factor. It might multiply the motion by four, while dividing the force by four.

The patient has his own hand-held control unit for switching the vacuum pump on or, on the other hand, for slowly venting the cylinder of vacuum. The patient can adjust the system until a gauge on the hand-held unit indicates the desired level of pulling force, e.g. in pounds. An infinite number of settings are available, from zero to a design limit based on piston area and pump strength. The hand held control unit ca be under control of either the patient or the attending doctor, nurse or therapist.

The traction device is completely self-contained, requiring no external accessories. Its simplicity and ease of operation make it suitable for home or unattended use.

The traction unit may include a manual mechanical vent for a faster release of vacuum from the cylinder, when desired. This can act as a safety feature, or simply as a quick way to release the patient from the traction.

In one preferred embodiment, the hand-held remote unit has a simple spring-loaded bi-directional switch for increasing or decreasing traction. A push of the spring loaded switch in an upper direction will increase vacuum in the cylinder, increasing the pull on the traction line; pressure on the switch in a lower direction operates the slow vent. In either case, the patient can watch the force gauge as the switch is manipulated, to set the force at a selected level, or the patient can simply adjust the unit to a comfortable position.

The hand-held unit and associated circuitry may be arranged so that if a power failure occurs in the system, the traction pulling force on the patient will be released. However, there may be provided a reversing switch to enable the physician or other attendant to select a mode such as just described, or a reverse mode wherein traction pulling force remains applied in the event of a power failure. This can be important when patient's injuries and treatment are such that a sudden release of traction could be dangerous to the patient.

In an alternate embodiment of the invention, there is included a controller for allowing the patient or doctor to set the traction pulling device at a certain desired force level, which will be maintained under all circumstances (except power failure, in one form of this embodiment). Thus, even if the patient moves somewhat toward the foot of the bed, the unit will quickly adjust and again resume the desired level of force. Similarly, if the patient moves in the opposite direction, the added force will be released and the unit will again settle at the preset, desired level of traction force.

It is therefore among the objects of the invention to allow a traction patient to control traction pulling force, without the need to summon an attendant, and also to allow the patient to place himself in or remove himself from traction without requiring help. Similarly, the invention achieves a selectable level of pulling force without the use of a collection of assorted weights. These and other objects, advantages and features of the invention will be apparent from the following description of a preferred embodiment, considered along with the accompanied drawings.

DESCRIPTION OF PREFERRED EMBODIMENTS

Figure 1:
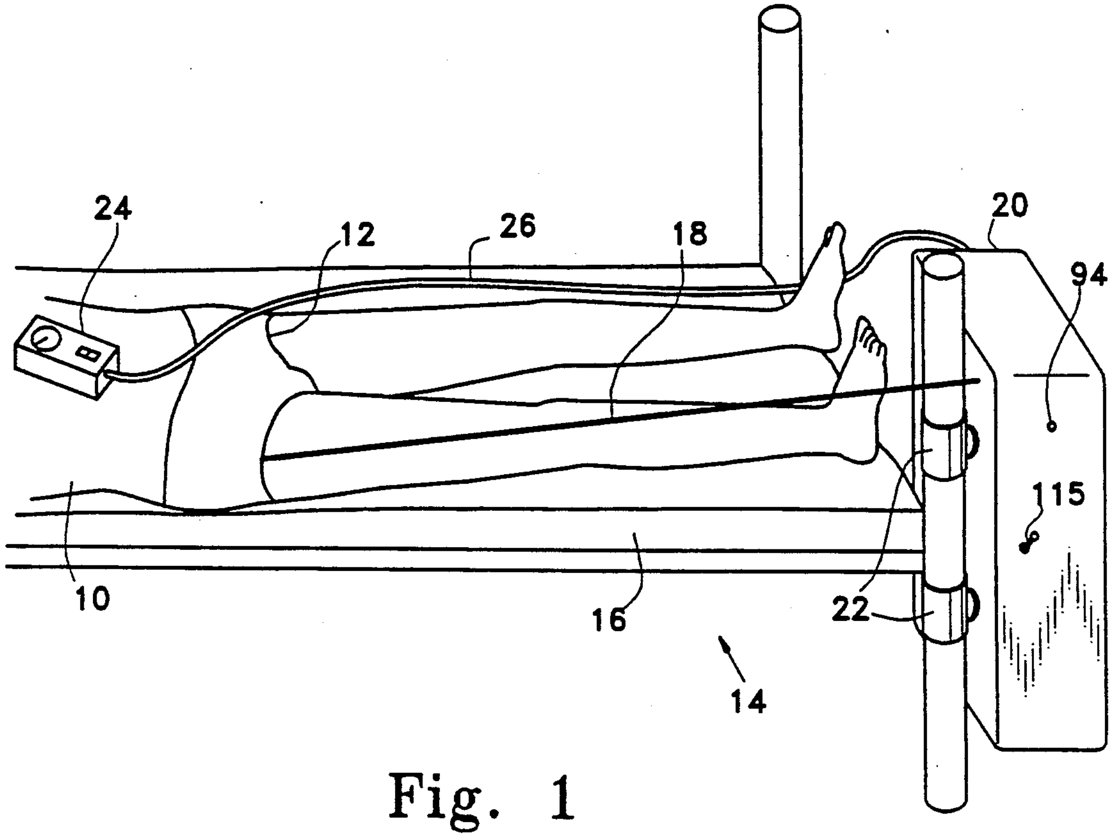
FIG. 1 is a view illustrating an automatic traction device in accordance with the invention, attached to the foot of a patient's bed for applying traction to a patient.

In the drawings, FIG. 1 shows a traction patient 10, in orthopedic or other therapeutic treatment, wearing a hip traction harness 12 and lying in a bed 14 with the lower end of the mattress 16 somewhat elevated.

The patient's traction harness 12 is connected by a rope or traction line 18 to a traction pulling unit 20 in accordance with the principles of this invention. The traction unit 20, which may be connected to a bedpost via ring type clamps 22 as shown, internally develops a pulling force in the line 18 under control of a hand-held remote control unit 24 which, as schematically indicated, is connected via a control line or cable 26 to the pulling unit 20.

The hand-held remote unit 24 may be under control of the patient, so that the patient sets the level of traction force and adjusts it as necessary and to avoid discomfort. This enables the device of the invention to be used in a patient's own home, unattended, or in a hospital or clinic with minimal attendance required.

Figure 2:
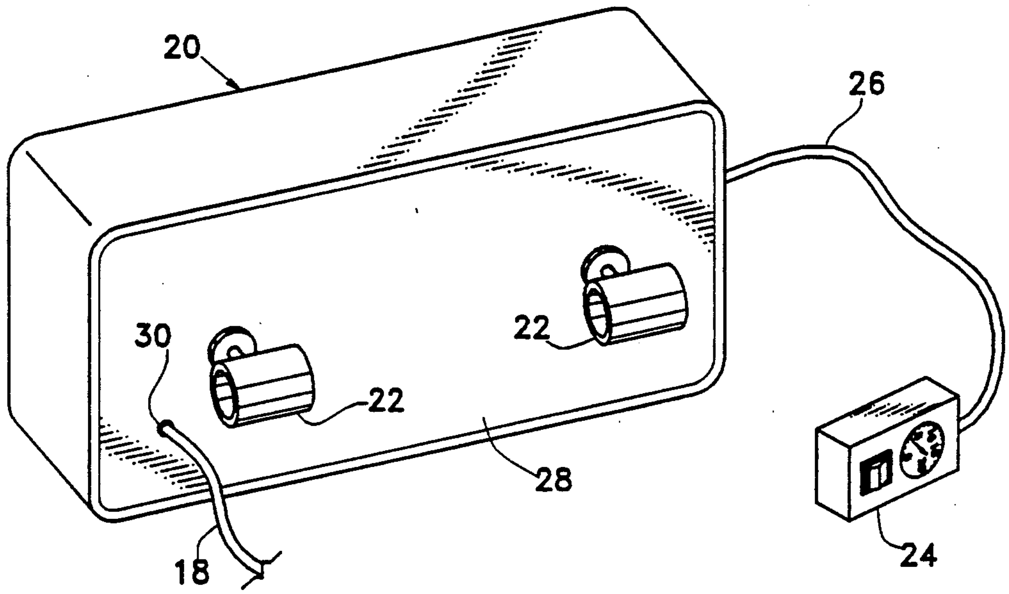
FIG. 2 is a perspective view further illustrating the traction unit shown in FIG. 1.

FIG. 2 shows the device of the invention, illustrating a back side 28 on which the clamps 22 are mounted. The traction line 18 extends from an outlet hole 30 at this side of the traction pulling unit 20. In a preferred embodiment, pulleys or rollers are included on all sides of the line 18, just inside the unit 20 on the other side of the outlet hole 30. This assures that the traction line 18 will operate smoothly, even at considerable angles from the normal position extending perpendicular from the back surface 28 of the unit.

FIG. 2 also shows the hand-held remote unit 24, connected to the traction pulling unit by the control cable 26 which, as more fully explained below, contains a pneumatic pressure-monitoring tube as well as electrical wiring in this embodiment. In a further embodiment described below, relating to an automatic force level maintaining feature, the cable contains only pneumatic tubing and n electrical wires.

Figure 3:
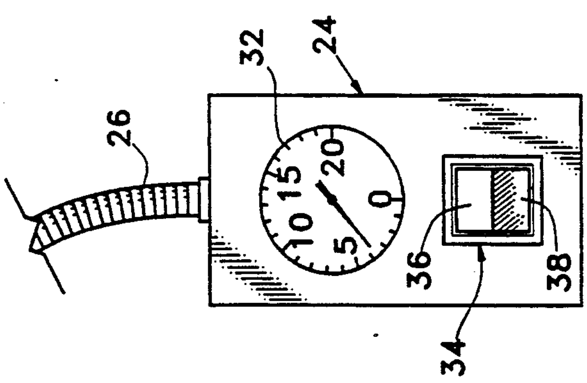
FIG. 3 is a plan view showing a remote control device for regulating the traction pulling force of the unit.

FIG. 3 shows the face of the hand-held remote unit 24 in greater detail. The face of the unit includes a force indicator gauge 32 which may be calibrated in pounds or kilograms of pulling force. In this preferred embodiment the patient control is provided by a simple spring-loaded switch 34 which is divided into an "increase" or "up" side 36 and a "decrease" or "down" side 38. Pressure by the patient on the upper side 36 will cause a vacuum pump in the pulling unit 20 to operate, thereby increasing the pulling force in the traction line 18 and showing this increasing force on the indicator gauge 32. The patient can increase force to the maximum force which is comfortable, or until a prescribed numerical value of traction force is shown on the gauge 32.

Similarly, the patient can operate the lower side 38 of the spring switch 34, which operates to gradually vent vacuum (or pressure) from the cylinder of the traction pulling unit 20. Again, decreases in force will immediately be shown on the force gauge 32.

Figure 4:
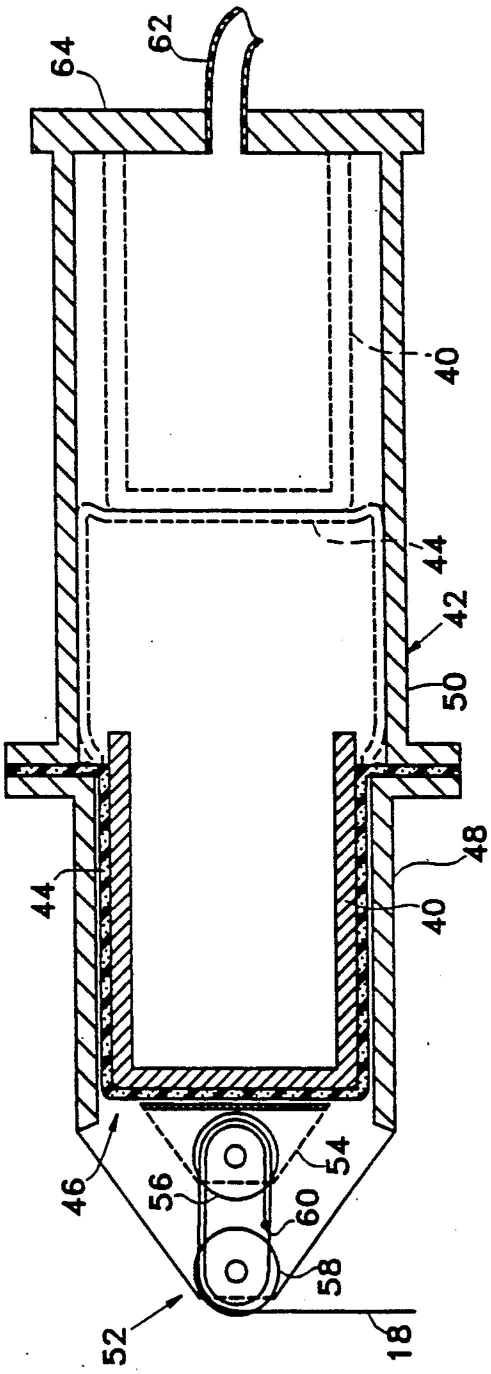
FIG. 4 is a schematic longitudinal sectional view showing a preferred type of piston and cylinder used in the device of the invention.

FIG. 4 schematically shows a cross section of a preferred piston and cylinder construction for the device of the invention. A piston 40 is movable to left or right as seen in the drawing within a cylinder 42. As illustrated a rolling diaphragm 44 is positioned between the piston and the head end 46 of the cylinder. As is well known, the rolling diaphragm establishes a completely leak-proof, airtight system which is important in the context of the present invention for holding a constant traction force on a patient. The rolling diaphragm is secured across the head end of the piston and engaged between sections 48 and 50 of the cylinder a shown.

Vacuum is applied at the left side of the piston, exerting force on the piston as determined by the piston's area. This force is applied ultimately to the traction line 18. It may be applied directly, or through a motion-multiplying device such as the block and tackle arrangement 52 shown in FIG. 4. By this arrangement, a bracket 54 secured to the head end of the piston supports a pair of pulleys 56, which work along with a pair of pulleys 58 secured to the cylinder housing to form the block and tackle. The end of the traction line 18 is secured to the cylinder housing at 60.

As a result, the motion in the line 18 induced by the movement of the piston is multiplied, while the force exerted in the line is divided by a similar factor such as four. This reduction, along with the area of the piston and the design limit to vacuum achievable by a vacuum pump of the system act together to place an absolute upper limit on the amount of pulling force which can be exerted on the traction patient.

An outlet line 62 is shown extending from a back or lower end 64 of the cylinder in FIG. 4. As will be seen below, this line 62 is the conduit through which vacuum is applied to the cylinder and through which it is vented from the cylinder when desired.

A spring (not shown) can be provided to pull or push the piston toward the released position (to the left in FIG. 4), but a spring is not required because with the vent open, pulling on the cord 18 will bring the piston to the released position.

Figure 5:
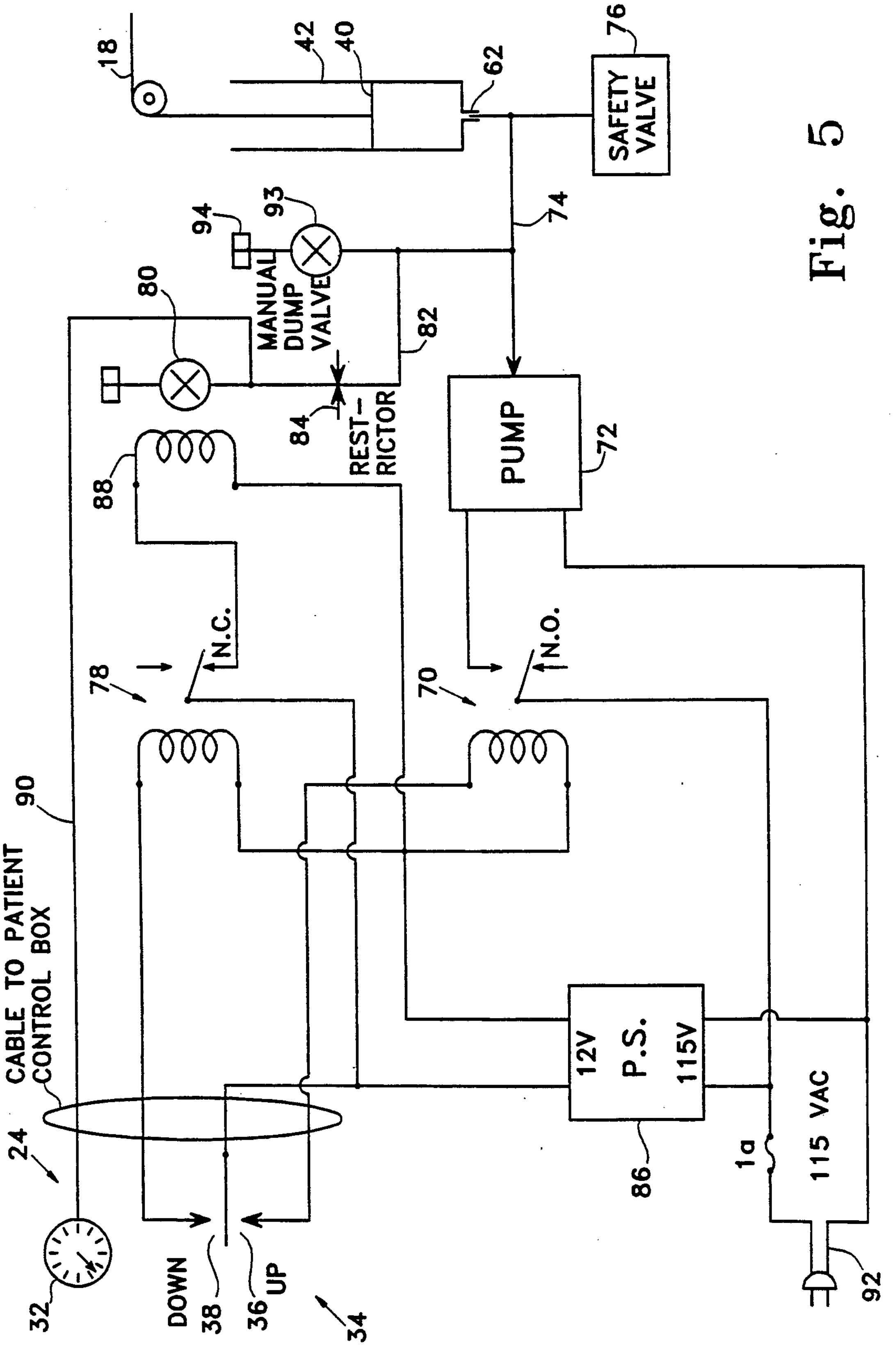
FIG. 5 is a schematic diagram illustrating the construction of the traction unit in one embodiment of the invention.

FIG. 5 is a schematic circuit and pneumatic diagram indicating a preferred construction for a system in accordance with the invention. In this schematic the system is shown in a valve closed position, so that vacuum is not being vented from the cylinder.

As can be seen from FIG. 5, when a patient or attending professional pushes the remote control switch 34 to engage the "up" switch contact 36 (in the upper left of the diagram, in the elements comprising the hand-held control device 24), this energizes a relay switch at 70. The normally open relay switch 70 is closed while the up switch is depressed, energizing a vacuum pump 72. The vacuum pump may be, for example, a model 113.163.600.0 pump manufactured by Wisa Corp. of Bayonne, N.J. This draws air through a line 74 leading to the outlet tube 62 of the cylinder 42.

As a further safety feature of the invention, a safety valve 76 may be included for preventing the vacuum level from exceeding a prescribed limit.

Further, a manually adjustable pressure or vacuum relief valve (not shown) may be included in the hand held unit 24, and connected to the pressure sensing tube 90 at the gauge. This would allow the upper limit of pull to be preset as an additional safety feature. If it is not desired to give control of the safety relief setting to the patient, the safety valve 76 in the main unit 20 can be relied upon for this safety feature. The safety relief valve 76 in the main unit can be externally settable (not shown) if desired.

The small vacuum pump 72 pulls air from the cylinder 42 drawing the piston 40 and pulling the traction line 18 to increase the traction force, until the "up" spring switch 36 is released. At that point, the relay switch 70 is released and returns to its normally opened position as shown in the drawing.

From FIG. 5 it can also be seen that if the "down" spring switch 38 is engaged, this operates a normally closed relay switch 78. The normally closed relay 78 normally holds a solenoid bleed valve 80 in a closed position, thereby holding vacuum in the traction force cylinder and not venting the cylinder. FIG. 5 shows that a vacuum line 82 leads to the vacuum line 74 from the pump 72 in a tee connection. A restrictor, schematically indicated at 84, may be included in the vacuum line 82 for the slow venting bleed function. Alternatively, the venting bleed valve 80 can include a restrictor itself.

The engagement of the pressure-lowering "down" switch 38 thus opens the relay 78 by closing a circuit which includes a power supply 86, producing, for example, 12 volts DC current. This releases a solenoid 88 which otherwise keeps the "normally open" solenoid bleed valve 80 closed. The bleed valve 80 opens, slowly venting pressure from the cylinder via lines 74 and 82, to atmosphere. The vacuum level in the cylinder, as well as the traction pulling force, are decreased until the spring switch 38 is released, causing the solenoid bleed valve 80 to again close.

If for safety reasons it is desirable to have only low voltage power in the unit, the power supply may comprise a U.L. approved power supply unit which plugs into a wall outlet, with only 12 volts or 24 volts, for example, going to the traction device 20.

FIG. 5 also shows a vacuum line 90 extending from a tee connection in the vacuum line 82 toward the force gauge 32 of the hand-held remote unit 24. This line 90 communicates the vacuum level in the cylinder to the gauge 32, which is calibrated to translate the vacuum level signal into pounds of force as seen in the traction line 18.

The hand-held unit and the circuitry as shown in FIG. 5 are arranged so that if a power failure occurs in the system at line power 92 or in the internal power supply 86, the traction pulling force on the patient will be released. As mentioned above, the solenoid bleed valve 80 is of the normally open type, but held closed by the solenoid 88 so long as power is supplied from the power supply 86 through the normally closed relay switch 78. When power is lost, the bleed valve vent 80 will vent vacuum and gradually release traction force. This is the usually desired mode, particularly for patients using the device of the invention at home. However, it is within the principles of the invention that the system can work within the reverse mode—that is, with a solenoid bleed valve which is normally closed and an operating relay 78 which is normally open. This might be desirable in situations where the patient's therapy would be endangered if traction force were to be released, and it is discussed further below in connection with FIG. 8.

FIG. 5 also shows a manual dump valve 93 which preferably is included in the system, as discussed above. This dump valve has a release button 94 on the outside of the traction unit 20 (such as shown in FIG. 1), for enabling a quick release of the traction force from the patient. This can be used as a safety quick release, or simply a faster way to release the patient whenever desired.

Further, there may be a mode reversal switch included in the system (not shown in FIG. 5), which will enable the doctor or other professional to reverse the mode from retaining vacuum in the event of a power failure, to releasing vacuum in the event of a power failure. This is the subject of FIG. 8 described below.

Figure 6:
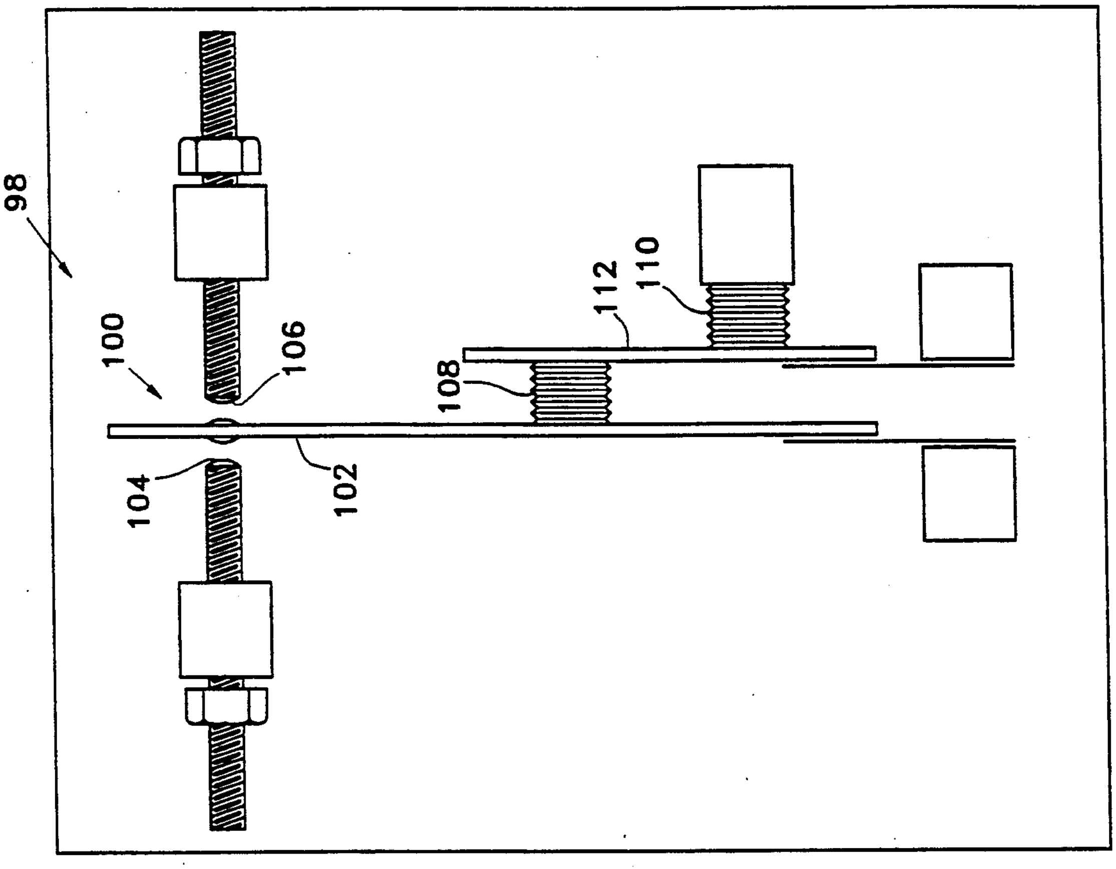
FIG. 6 is a schematic view showing an automatic controller which may be used in accordance with the invention, for enabling setting and maintaining of a certain traction force regardless of movements of the patient.
Figure 7:
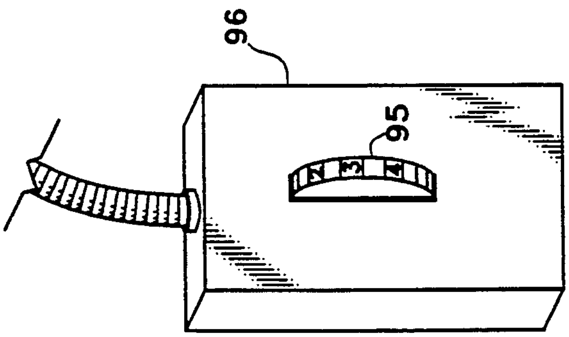
FIG. 7 is a perspective view showing the exterior of a patient-held remote control unit which is connected to the controller illustrated in FIG. 6.

FIGS. 6 and 7 show an optional differential controller which can be employed in the system of the invention, essentially replacing the bi-directional spring switch 34 shown in FIGS. 3 and 5.

FIG. 7 shows one example of a type of traction force selector dial or wheel 95 which may be included in a hand-held remote controller unit 96. This enables the patient or the attending professional to select a level of traction pulling force, as indicated on the dial 95. Force level is shown on the selector dial, so that no needle gauge is needed. The differential controller device will then adjust the system to the appropriate pulling force. An adjustment will occur at any time the selector dial 95 is adjusted, or at any time the patient moves toward or pulls away from the traction unit, so that the system will "follow" the patient's movements and readjust the pulling force to the selected force each time a change occurs.

FIG. 6 shows a simple form of differential controller preferred for use with the present invention.

The controller mechanism 98 includes a contact switch 100 which, when moved to the left as seen in FIG. 6, will engage a center contact 102 against a contact 104 that turns on the vacuum pump (equivalent to engaging the "up" switch in FIG. 5). When moved to the right, the center contact 102 will engage a contact 106 which effects the venting of pressure from the vacuum cylinder (equivalent to engaging the "down" switch in FIG. 5). The contact 102 and a contact stem 103 are configured to float in a centered position at equilibrium.

An upper vacuum bellows 108 is connected by a vacuum line 109 to vacuum cylinder pressure, which may be through the line 74, for example, shown in FIG.

5. A lower bellows 110 is a pressure bellows and is connected by a line 111 into the patient's hand-held unit 96, which includes another small pressure bellows (not shown) which is responsive to the force level at which the patient's dial 95 is set. Adjustment of the dial 95 will contract or expand the bellows in the remote unit 96, thus increasing or decreasing pressure in the line leading to the differential controller bellows 110. A simple cam arrangement can be included in the unit 96 to squeeze the bellows when the dial is turned.

Thus, if the patient reduces the amount of force on his settable indicator, this will reduce pressure in the remote unit bellows which is not illustrated, and will call for a decrease in vacuum in the traction unit cylinder. Such an adjustment will cause the lower bellows 110 to deflate somewhat, thereby contracting somewhat. This moves the contact 102 at the top of the controller to the right, engaging the contact 106 and operating a solenoid valve of the traction unit to vent pressure from the cylinder. This can be through a relay, such as the relay 78 shown in FIG. 5, opening a normally closed circuit to effect the opening of a solenoid bleed valve 80 such as shown in FIG. 5. Alternatively, it can directly open a solenoid bleed valve (not shown) which is normally closed when power is not applied. That is, the system can be set up to either continue traction in a power failure situation or to release traction in a power failure situation, as generally described with reference to FIG. 8 below.

Eventually, pressure will be vented from the traction unit cylinder due to the engagement of the contact 106, and the upper bellows 108 shown in FIG. 6 will contain a lower level of vacuum, i.e. a higher pressure, and will expand. This will again neutralize the position of the center contact 102, to a position between the two actuating contacts 104 and 106. Equilibrium will have been reached, at the force level selected by the patient using the remote controller device 96.

If the patient or attendant wishes to increase traction force, he selects a higher numerical force level on the selector dial 95 of the hand-held remote device. This increases pressure in the internal bellows of the hand-held device 96, increasing pressure in the lower bellows 110 of the differential controller as shown in FIG. 6. This causes to occur the reverse of what was explained above. The increased pressure in the bellows 110 pushes the contact assembly to the left, with the upper bellows 108 transferring force from a plate 112 to the stem 103 and center contact 102, which then engages the left contact 104. This causes the vacuum pump 72 (FIG. 5) to be actuated, and this may be through a relay switch similar to the relay 70 shown in FIG. 5. Vacuum level is increased in the main cylinder, which is communicated to the upper bellows 108 of the differential controller. The upper bellows 108 therefore contracts when a certain level of vacuum has been reached in the main cylinder, causing the center contact 102 to move right and again to the centered position and shutting off the vacuum pump 72. Again, equilibrium is reached at the increased level of force.

It is therefore seen that with the differential controller set to a prescribed traction force level, the patient can move around in the bed and traction force will readjust to the set level. If the patient pulls away from the traction unit, this temporarily increases the force and also the vacuum level, which acts to readjust vacuum downward through the differential controller. The opposite occurs if the patient moves toward the unit.

Figure 8:
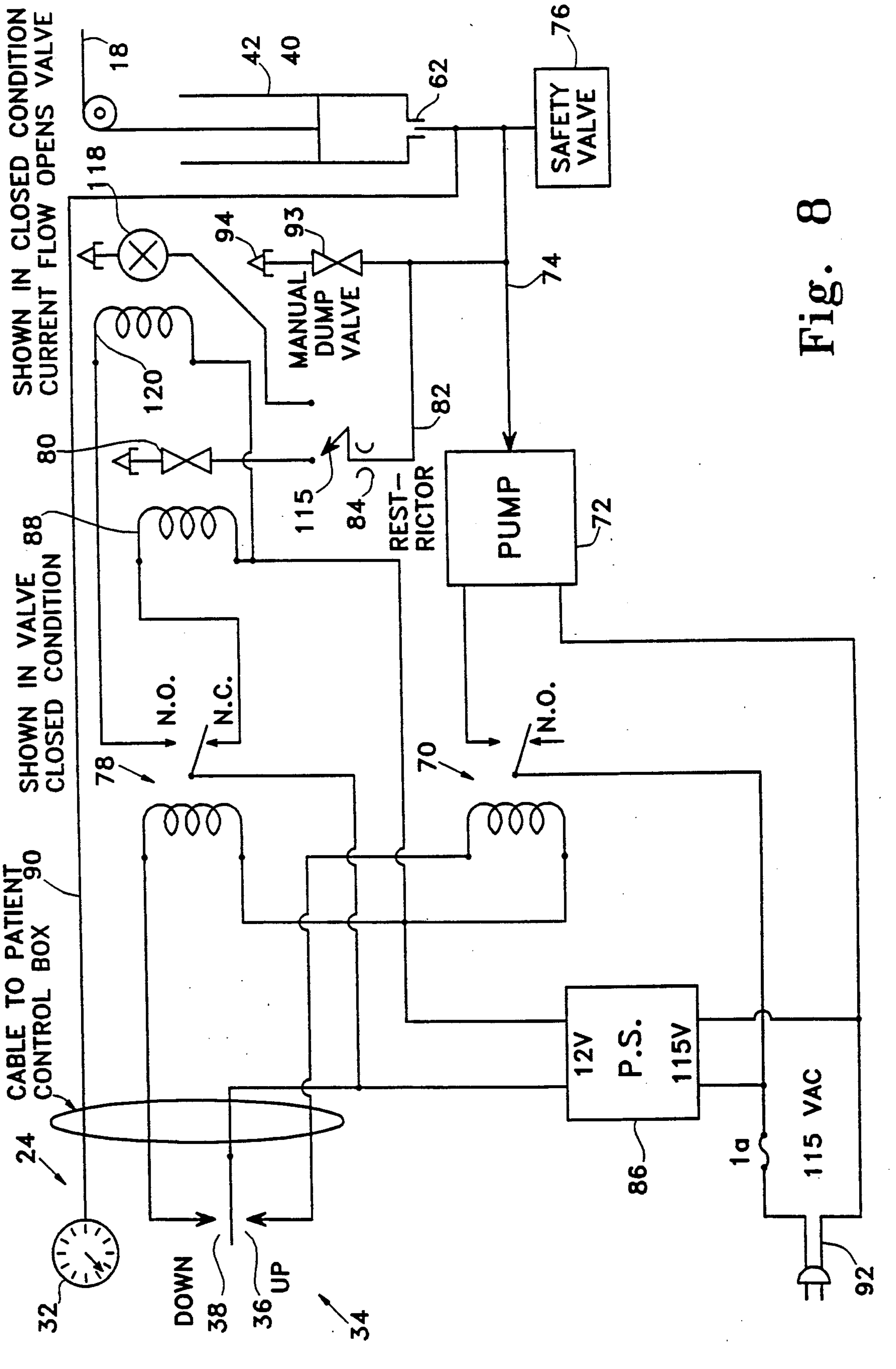
FIG. 8 is a schematic diagram similar to FIG. 5 but showing a modification which enables switching of a fail-safe mode of the traction apparatus.

In the embodiment shown in FIG. 8, there is provided a manual toggle valve 115 which operates a venting valve 80 similar to the valve 80 described above, and a second vent valve 118, operated by another solenoid coil 120, which when energized opens the valve. In other words, the valve 118 is normally in the closed position, in the absence of power. The system as configured with the valve 115 position shown in FIG. 8 is functionally the same as what is shown in FIG. 5. In a power loss the solenoid coil 88 is no longer powered, and the valve 80, biased toward opening, will open and vent the system to release traction force.

However, when the manual toggle valve 115 is switched over to the second venting system, i.e. to the vent valve 118, this changes the system to a configuration in which traction force will be maintained in the even of a power failure. Since the solenoid vent valve 118 is biased toward the closed position (open only when current flows through the solenoid coil 120), a power failure preventing energization of the coil 120 will have no effect on the vacuum level.

In normal operation when the system of FIG. 8 has power, it will operate as described above. The operation when the manual toggle valve 115 is to the left as shown in FIG. 8 is the same as in FIG. 5, already described. With the manual toggle valve 115 of FIG. 8 switched to the right, to the venting valve 118, it is easily seen from FIG. 8 that a closing of the "down" switch 38 in the control 34 will energize the solenoid switch 78 to move the contact to close in the "normally open" position. This has the effect of energizing the coil 120 to open the valve 118, adjusting the traction pulling force downwardly. In the same situation, if the "up" contact 36 is energized, this again closes the solenoid switch 70 to activate the vacuum pump 72, thereby increasing traction pulling force.

The manual toggle valve can be on the exterior of the main housing of the traction device, such as indicated at 115 in FIG. 1.

In some embodiments of the invention, rather than the tension indicator described, which uses vacuum pressure to operate a calibrated device to indicate pulling force, simpler or more mechanical devices can be used. For example, a tension spring could be placed directly in the traction cord 18 and in parallel with the tension spring a linear potentiometer which feeds a signal back to the electrical controls to provide, for example, a digital readout of force. The signal from the potentiometer could also be a part of the controlling mechanism for keeping the force within a prescribed window. The signal can be balanced against the control signal coming from the patient's remote device, which in this case would be a potentiometer putting out a voltage signal.

A simple device for indicating pulling force could be a simple spring scale or fish scale inserted in the traction pulling cord and producing a direct reading of force in the cord. Pulling force sensing could also be accomplished using a strain gauge or other electromechanical force sensing device such as a load cell, P.Z.T. positioned in the cord for generating an indication of pulling force. As is known to those skilled in the art, such a strain gauge can be fed into a differential operational amplifier to provide a function which can be used to control the pulling force within a desired range.

It should also be understood that the invention is not limited to the piston and cylinder shown and described. The origin of the pulling force could be a bellows, diaphragm or other pneumatic device. Similarly, air pressure could be used rather than vacuum force to operate on a piston, bellows, etc.

The above described preferred embodiment is intended to illustrate the principles of the invention, but not to limit its scope. Other embodiments and variations to this preferred embodiment will be apparent to those skilled in the art and may be made without departing from the spirit and scope of the invention as defined in the following claims.

I claim:

1. An apparatus for producing a selected and adjustable level of traction pulling force, particularly for a medical traction patient, comprising, piston and cylinder means with pump means for exerting a pressure and a force on the piston, which is positioned within the cylinder, a tension line connected to the piston in a position so as to be pulled in tension when the piston is moved by the pressure, venting means associated with the cylinder for selectively releasing the pressure on the piston, remote control means for operation by a patient or physician, for selectively activating the pump means or the venting means in order to increase pulling force in the line or to decrease pulling force in the line.

2. The apparatus of claim 1, further including force gauge means as a part the remote control means, for indicating numerically to the patient or physician the amount of pulling force in the tension line.

3. The apparatus of claim 2, wherein the pump means comprises a pneumatic pump and wherein the force gauge means includes calibrated pneumatic pressure-responsive means for indicating force as a function of pressure level at the piston.

4. The apparatus of claim 1, wherein the piston and cylinder include a leak proof rolling diaphragm, for preventing any leakage from affecting pressure exerted by the piston on the tension line, whereby a force in the tension line will be maintained over a period of time.

5. The apparatus of claim 1, wherein the pump means comprises a pneumatic vacuum pump acting on a suction side of the piston, with said pressure being exerted by atmospheric pressure on an opposite side of the piston.

6. The apparatus of claim 5, wherein the piston and cylinder include a leak proof rolling diaphragm, for preventing any leakage from affecting pressure exerted by the piston on the tension line, whereby a force in the tension line will be maintained over a period of time.

7. The apparatus of claim 1, further including settable differential controller means associated with the remote control means for enabling a person to selectively set a given pulling force for the apparatus, and for automatically controlling the pressure and the venting of the cylinder to effect said selected pulling force.

8. The apparatus of claim 7, wherein the settable differential controller means includes means for reestablishing a set level of pulling force even when a traction patient connected to the tension line moves in a direction of pulling on the tension line or in a direction of slackening the tension line.

9. The apparatus of claim 1, wherein the pump means comprises a pneumatic vacuum pump acting on a suction side of the piston, with said pressure being exerted by atmospheric pressure on an opposite side of the piston, and further including mode switch means associated with the venting means for selectively and manually setting the apparatus to vent vacuum and release traction force in the event of a loss of electrical power to the apparatus, or to retain vacuum and traction force in the event of a loss of electrical power to the apparatus.

10. The apparatus of claim 9, wherein the mode switch means comprises a first solenoid operated venting valve which is normally open but closed when current flows through a solenoid of the solenoid operated venting valve, and a second solenoid operated venting valve which is normally closed but open when current flows through a second solenoid of the second solenoid venting valve, and further including a manual toggle valve communicating with the suction side of the piston and manually switchable between a position wherein the suction side of the piston is connected to the first solenoid operated venting valve, or a position wherein the suction side of the piston is connected to the second solenoid operated venting valve, and further including an electrical switch movable between a position supplying power to the first solenoid operated venting valve and a different position removing current from the first venting valve and supplying current to the second solenoid operated venting valve, the electrical switch being biased normally toward said first position, whereby movement of the electrical switch from the first position to the second position will vent the suction side of the piston, regardless of the position of the manual toggle valve.

* * * * *